United States Patent [19]

Lovell

[11] Patent Number: 5,143,539
[45] Date of Patent: Sep. 1, 1992

[54] METHOD AND COMPOSITION FOR PROTECTING PLANTS AGAINST INJURY FROM THE INTERACTION OF AN ORGANOPHOSPHATE INSECTICIDE-NEMATICIDE AND AN AHAS INHIBITING HERBICIDE

[76] Inventor: James B. Lovell, 99 Woosamonsa Rd., Pennington, N.J. 08534-3804

[21] Appl. No.: 690,188

[22] Filed: Apr. 18, 1991

[51] Int. Cl.$^5$ .............. A01N 43/54; A01N 41/10; A01N 57/10; A01N 31/08

[52] U.S. Cl. .................... 71/92; 71/88; 71/103; 71/122; 514/89; 514/127; 514/132; 514/140; 514/141

[58] Field of Search ............... 71/87, 92, 122, 103, 71/88; 514/141, 89, 127, 132, 140; 252/404

[56] References Cited

U.S. PATENT DOCUMENTS

| | | |
|---|---|---|
| 4,936,901 | 6/1990 | Surgant, Sr. et al. ............ 71/92 |
| 4,956,129 | 9/1990 | Scher et al. ................. 264/4.7 |

OTHER PUBLICATIONS

Ogawa et al. CAS 111: 189,595x. "Herbicidal method using sulfonormides, surfactants, and oils or hydrocarbons." 1989.

Kimura et al. CAS 112: 173,972c "SL-950 [nicosulfuran], a novel sulfonylurea herbicide for corn." 1989.

Orr et al. In Moreland et al. *Biochemical Responses Induced by Herbicides.* "Proposed site(s) of action . . . " 1982. pp. 131–152.

Veselovskii. CAS 97: 106,982q. "Role of bioantioxidants in the survival of plants under unfavorable conditions." 1982.

*Primary Examiner*—Allen J. Robinson
*Assistant Examiner*—S. Mark Clardy

[57] ABSTRACT

There is provided a method for inhibiting or preventing injury to a plant caused by the synergistic interaction of an organophosphate compound employed for the protection of the plant against attack by insects and nematodes and the use of an acetohydroxacid synthase (AHAS) inhibiting compound employed for the control of undesirable weed species in the locus of the plant comprising the application of an effective amount of an antioxidant.

17 Claims, No Drawings

METHOD AND COMPOSITION FOR PROTECTING PLANTS AGAINST INJURY FROM THE INTERACTION OF AN ORGANOPHOSPHATE INSECTICIDE-NEMATICIDE AND AN AHAS INHIBITING HERBICIDE

DESCRIPTION OF THE INVENTION

This invention relates to methods and compositions for eliminating or preventing injury to a crop plant caused by the interaction of two or more pesticides applied to the plant in combination, either simultaneously or sequentially. Of particular concern are synergistic responses which occur on a single plant species. Synergistic responses obtained with combinations of herbicides, insecticides and fungicides are described as the combined action of two components of a mixture such that the total effect is greater or more prolonged than the sum of the effects of the two components taken independently.

More particularly, the invention provides methods and compositions for eliminating or preventing injury to a crop plant resulting from the interaction of an organophosphate pesticide being taken into the root system of the plant prior to, or simultaneously with, the absorption of an acetohydroxyacid synthase (AHAS) inhibiting herbicide. More particularly, this invention relates to methods of and compositions for preventing, inhibiting or ameliorating injury to plants resulting from the interaction of O,O-diethyl S-[(ethylthio)methyl]phosphorodithioate (phorate) or O,O-diethyl S-{[(1,1-dimethylethyl)thio]methyl)phosphorodithioate (terbufos) being taken into the root system of plants prior to, or simultaneously with, the absorption of a sulfonylurea such as 1-(4,6-dimethoxypyrimidin-2-yl)-3-(3-dimethylcarbamoyl-2-pyridylsulfonyl)urea (nicosulfuron) or 2-[4,6-bis(difluoromethoxy)pyrimidin-2-ylcarbamoylsulfamoyl]benzoic acid (primisulfuron) or an imidazolinyl nicotinate such as imazethapyr or imazamethapyr or an imidazolinyl quinolinecarboxylate such as imazaquin.

The ever increasing demands for greater quantities and improved quality of food to feed the pyramiding human population around the world has driven plant science agriculturalists to maximize crop yield and product quality for every hectare of land under cultivation. To this end, knowledgeable farm practitioners have found it advantageous to protect their crops from the time of planting through harvest and beyond against attack, infestation or encroachment by all types of pests including: insects, acarina, bacteria, fungi, nematodes and undesirable plant species. Thus, to achieve the desired protection it has become a rather common practice in the farming industry to use a multiplicity of pest control agents, applied either simultaneously or sequentially, to provide concurrent and continuous protection for the treated crop plant against injury from this multiplicity of pests.

In many instances, it has been found that combination treatments afford plant protection against a variety of pests with a single application of combined pesticides or with simultaneous or sequential applications of two or more pesticides applied to the planted and/or growing crop In practice, there are many known instances of considerable modifications in the biological activity of one pesticide brought about by the prior, simultaneous or sequential application of another pesticide to the same target species. When this occurs it is commonly referred to as an "interaction". As a result of pesticide interactions, adverse effects can occur and the responses of target species such as crop plants to combined applications of two or more pesticides are not predictable from the effect of each pesticide applied alone. Said interactions are described as antagonistic when the net effect is a decrease in the biological activity and synergistic when the net effect is an enhancement of biological activity. In other words, a synergistic interaction of a pesticide combination is a substantially more than additive toxic action of two or more pesticides when used together. Pesticide combination applications which result in a synergistic interaction are herein described as synergistic pesticide combinations.

For the past two decades, terbufos and phorate have been used for the control of soil-borne pests and as systemic insecticides. These compounds have been used successfully for the control of soil-borne and leaf-feeding pests and have been utilized in conjunction with a variety of other pesticides without reports of undesirable interactions. Thus, it is surprising to find that with the recent introduction of certain AHAS inhibiting herbicides (for instance, sulfonylureas such as nicosulfuron and primisulfuron) there appears to be a synergistic interaction observed in corn plants which have been treated at planting with a soil insecticide such as disulfoton, chlorpyrifos, bentazone, fonofos, phorate or terbufos and thereafter treated early postemergence or when the plants are in the seedling stage, i.e. about the three to five leaf stage, with nicosulfuron or primisulfuron.

It is believed that the synergistic interaction of certain organophosphate compounds with nicosulfuron or primisulfuron occurs when an organophosphate compound is taken into the root system of a plant and inhibits the plant,s ability to metabolize the sulfonylurea compound. This inhibition permits the sulfonylurea compound to accumulate in the plant tissue and reach levels which can cause significant injury to the plant.

It has also been found that the interaction of the organophosphate and the sulfonylurea occurs only when the organophosphate is the first chemical to be taken into the plant. If the organophosphate is translocated to the growing points of the plant, i.e. the meristematic tissue, before the sulfonylurea is taken into the plant, it inhibits the metabolism of the sulfonylurea and injury occurs; whereas, when the sulfonylurea is translocated to the meristematic tissue of the plant before the organophosphate arrives, injury is essentially avoided.

It is therefore an object of this invention to provide methods and compositions for inhibiting, preventing or ameliorating injury of a plant resulting from the synergistic interaction of two or more chemicals applied to said plant or the locus in which it is planted or growing.

It is also an object of this invention to provide methods and compositions for inhibiting or preventing injury of a plant resulting from the interaction of an organophosphate compound being taken into a plant prior to, or simultaneously with, the intake of a sulfonylurea compound.

A further object of this invention is to provide methods and compositions for protecting a crop plant from attack by soilborne pests and preventing incursion into the crop growing area of undesirable plant species while inhibiting or preventing injury to the crop plant due to the synergistic interaction between O,O-diethyl S-{[(1,1-dimethylethyl)thio]methyl}phosphorodithioate (terbufos) and nicosulfuron or primisulfuron, when these compounds are applied simultaneously or sequentially to recently planted or growing crops.

Surprisingly, it has been found that the above objectives can be achieved through the application of an antioxidant such as butylated hydroxytoluene (BHT), butylated hydroxyanisole (BHA), tert-butylhydroquinone (TBHQ), 6-ethoxy-1,2-dihydro-2,2,4-trimethylquinoline (ethoxyquin), ascorbic acid or the like to (1) the furrow and/or the seed or propagating organ being planted, (2) the soil in which the crop is planted or growing, (3) the pesticide composition being applied to the furrow or soil surface in which the crop is being planted or growing or (4) the soil between the seed, propagating organ or root system of of the plant which is to be protected from soilborne pests and incursion of undesirable plant species into the crop growing area.

In practice, the antioxidant may be applied to the soil pesticide composition by topcoating said compositions with a spray or dust containing the antioxidant or it may be applied directly to the seed as a seed coating or it may be applied to the soil surface or in the furrow in which the seed or propagating organ is planted Alternatively, the seed or granulated pesticide composition may be coated with a 5% to 50% wettable powder composition of an antioxidant.

It is also contemplated that the antioxidant be premixed with the active ingredient prior to the formulation of the soil insecticide-nematicide. The premixture can be applied directly to a suitable carrier such as clay, attapulgite, BIODAC®, montmorillonite and the like, or may be homogeneously mixed with a plastic formulation such as a polyvinyl chloride or a starch-like formulation.

Compositions are provided in which an effective amount of an antioxidant is intimately dispersed in an inert carrier or liquid diluent. An inert carrier is one that will not react with the antioxidant and is suitable for agronomic use.

Typical compositions of the invention include wettable powders, dusts, granules, sprays and the like in which the antioxidant is present in relatively large amounts and which are suitable for application to the soil, pesticide composition or plant seed either directly or after an intermediate dilution or blending step.

In order to facilitate a further understanding of the invention, the following examples are presented primarily for the purpose of illustrating certain more specific details thereof. The invention is not to be deemed limited thereby except as defined in the claims.

EXAMPLE 1

Evaluation Of The Effect Of An Antioxidant On The Inhibition Or Prevention Of Crop Injury Due To The Synergistic Pesticide Interaction Of An Organophosphate Insecticie-Nematicide And An AHAS Inhibiting Herbicide The organophosphate insecticide-nematicide used in this experiment is terbufos, present as a commercial granular formulation containing 15% wt/wt of active ingredient (COUNTER® 15G) and as a commercial controlled release formulation containing 20% wt/wt of active ingredient (COUNTER® 20CR). The AHAS inhibiting herbicide used in this experiment is a sulfonylurea, primisulfuron, present as a commercial formulation containing 75% wt/wt active ingredient (BEACON® 75 WG).

The antioxidant, butylated hydroxytoluene (BHT), is dissolved in methylene chloride to give solutions of concentrations ranging from 1.2% to 40%. Preweighed samples of COUNTER® 15G and COUNTER® 20CR are placed in a Ty-Nee® tumbler, model 1600 and rotated. The solutions of BHT are atomized, using a DeVilbiss atomizer, onto the rotating COUNTER® granules to achieve a BHT coated granular product containing a final ratio of from 1:1 to 5:1 terbufos (active ingredient) to BHT (antioxidant).

Six inch azalea pots are filled with Wisconsin silty loam soil and lightly watered. A furrow, 1 1/2 inches deep by 5 1/4 inches long, is impressed into the soil in each pot. Into the furrow are placed two corn seeds and from 0 to 99 mg of treated and untreated COUNTER® granules The soil insecticide is added in-furrow at rates equivalent to the recommended label rates for the control of insects and nematodes. The furrows are closed by hand and the pots are watered, placed under high intensity discharge lamps in the greenhouse and cared for in the usual manner commensurate with standard greenhouse practice.

When the corn plants have reached the 3rd to 4th leaf stage they are sprayed with a solution of BEACON® 75WG containing 0.25% ORTHO® X-77, a surfactant manufactured by Chevron Chemical Inc., using a stationary nozzle at 40 psi at a rate sufficient to obtain the equivalent of 0.040 kg per hectare of primisulfuron. After spraying, the plants are placed in the greenhouse and cared for as described above. Plant height is recorded prior to the spraying on the day of herbicide application and at regular intervals thereafter. Each treatment is replicated five times.

The data obtained are analyzed and the mean plant height is reported in Table I.

TABLE I

Evaluation Of The Effect Of An Antioxidant On The Injury Caused By The Interaction Of A Combination Insecticide/Herbicide Application

| In-Furrow Insecticide Treatment | Herbicide Rate (kg/ha) | Mean Plant Height (cm) Days After Herbicide Application | | | | | | | |
|---|---|---|---|---|---|---|---|---|---|
| | | 0 | 5 | 11 | 14 | 17 | 19 | 21 | 24 |
| Untreated Check | 0 | 15.8 | 36.0 | 49.2 | 55.8 | 63.9 | 66.6 | 67.4 | 77.7 |
| Untreated Soil | 0.04 | 16.5 | 34.9 | 47.5 | 54.2 | 60.9 | 62.9 | 66.4 | 72.4 |
| COUNTER-15G | 0.04 | 12.1 | 18.0 | 20.1 | 24.0 | 31.7 | 33.4 | 39.9 | 51.2 |
| COUNTER-15G[1] + BHT | 0.04 | 13.4 | 20.2 | 38.5 | 48.6 | 62.4 | 65.9 | 68.6 | 76.3 |
| COUNTER-20CR | 0.04 | 11.5 | 18.9 | 30.5 | 34.8 | 48.1 | 51.9 | 55.3 | 61.2 |
| COUNTER-20CR[2] + BHT | 0.04 | 10.8 | 21.9 | 40.3 | 51.1 | 62.7 | 68.2 | 71.0 | 80.9 |

[1]Ratio of terbufos to BHT is 1:1.
[2]Ratio of terbufos to BHT is 5:1

EXAMPLE 2

Evaluation Of The Effect Of An Antioxidant On The Prevention Or Inhibition Of Crop Injury In The Field Field plots are planted with corn seed and COUNTER ®, formulations of terbufos are applied infurrow at rates of from 0 to 8 oz. per 1,000 row-ft. COUNTER ® 15G, treated and untreated, is applied at 8 oz per 1,000 row-ft and COUNTER ® 20CR, treated and untreated, is applied at 6 oz per 1,000 row-ft. The COUNTER ® formulations are treated with butylated hydroxytoluene or butylated hydroxyanisole as described in Example 1.

When the plants have grown to the 2nd to 3rd leaf stage, BEACON ® 75WG is applied postemergence at such a rate as to obtain the equivalent of 0.032 kg/ha of primisulfuron. Ten plants per plot are preselected for monitoring of plant height at 7 day intervals following the postemergent herbicide application. Each treatment is replicated two times.

Plant height (the distance from the ground to the tip of the tallest leaf) is used as a general indicator of plant growth and vigor. The data obtained is analyzed and the mean plant height is recorded in Table II.

TABLE II

Field Evaluation Of The Effect Of An Antioxidant On Injury To Corn Due To A Synergistic Pesticide Interaction

| Treatment | Herbicide Rate kg/ha | Mean Plant Height (cm) 21 Days After Herbicide Application | |
|---|---|---|---|
| | | COUNTER-15G | COUNTER-20CR |
| Untreated Check | 0 | 55.3 | 55.3 |
| Untreated Soil | 0.032 | 51.0 | 51.0 |
| Untreated COUNTER | 0 | 50.6 | 57.7 |
| Untreated COUNTER | 0.032 | 36.8 | 38.1 |
| 3.2–3.6% BHT[1] | 0.032 | 33.6 | 47.1 |
| 3.2–3.6% BHA | 0.032 | 43.3 | 46.0 |
| 0.9–1.2% BHT[2] | 0.032 | 30.9 | 42.6 |
| 0.9–1.2% BHA | 0.032 | 35.8 | 44.6 |

[1]COUNTER-15G treated with 3.6% wt/wt; COUNTER-20CR treated with 3.2% wt/wt
[2]COUNTER-15G treated with 0.9% wt/wt; COUNTER-20CR treated with 1.2% wt/wt

I claim:

1. A method for the inhibition, prevention or amelioration of injury to a crop plant resulting from the interaction of an organophosphate systemic soil pesticide and an acetohydroxyacid synthase inhibiting herbicide applied to the crop plant or the locus in which it is planted or growing which comprises applying an antioxidant (1) to the soil in which the plant is planted or growing (2) to the seed or propagating organ of the crop plant (3) with the pesticide being applied to the soil in which the plant is planted or growing or (4) to the soil between the seed, propagating organ or root system of the crop plant.

2. The method according to claim 1 wherein the antioxidant is selected from the group consisting of butylated hydroxytoluene, butylated hydroxyanisole, tert-butylhydroquinone, 6-ethoxy-1,2-dihydro-2,2,4-trimethylquinoline and ascorbic acid.

3. The method according to claim 2 wherein the antioxidant is butylated hydroxytoluene or butylated hydroxyanisole.

4. The method according to claim 3 wherein the crop plant is corn and the pesticides are terbufos and a sulfonylurea herbicide.

5. The method according to claim 4 wherein the antioxidant is applied with the terbufos and the sulfonylurea herbicide is primisulfuron or nicosulfuron.

6. The method according to claim 5 wherein the terbufos is coated with the antioxidant and forms a granule.

7. The method according to claim 1 wherein the organophosphate soil pesticide is selected from the group consisting of terbufos, phorate, parathion, fonofos, disulfoton and chlorpyrifos.

8. The method according to claim 7 wherein the acetohydroxyacid synthase inhibiting herbicide is selected from the group consisting of sulfonylurea, imidazolinyl nicotinate, imidazolinyl quinolinecarboxylate and triazolopyrimidine.

9. The method according to claim 8 wherein the insecticide is terbufos and the herbicide is selected from the group consisting of primisulfuron, nicosulfuron, imazethapyr, imazamethapyr and imazaquin.

10. The method according to claim 9 wherein the herbicide is primisulfuron.

11. The method according to claim 9 wherein the herbicide is nicosulfuron.

12. The method according to claim 1 wherein the seed has been treated with the antioxidant.

13. A composition for the inhibition, prevention or amelioration of injury to a crop plant resulting from the synergistic interaction of two or more pesticides applied to the crop plant or the locus in which it is planted or growing which comprises one of the pesticides, an effective amount of an antioxidant and an inert carrier or liquid diluent.

14. The composition according to claim 13 wherein the antioxidant is selected from the group consisting of butulated hydroxytoluene, butylated hydroxyanisole, tert-butylhydroquinone, 6-1,2-dihydro-2,2,4-trimethylquinoline and ascorbic acid and the pesticide is terbufos or phorate.

15. The composition according to claim 14 wherein the antioxidant is butylated hydroxytoluene and the pesticide is terbufos.

16. The composition according to claim 14 wherein the antioxidant is butylated hydroxyanisole and the pesticide is terbufos.

17. The composition according to claim 13 wherein the pesticide is terbufos and the antioxidant coats the terbufos and is in the form of a granule.

* * * * *